US008609333B2

(12) United States Patent
Zhou et al.

(10) Patent No.: US 8,609,333 B2
(45) Date of Patent: Dec. 17, 2013

(54) DETECTION OF METHYLATED DNA AND DNA MUTATIONS

(75) Inventors: Chongwu Zhou, Arcadia, CA (US); Mark E. Thompson, Anaheim, CA (US); Allen S. Yang, Valencia, CA (US); Richard James Cote, Miami, FL (US)

(73) Assignee: University of Southern California, Los Angeles, CA (US)

( * ) Notice: Subject to any disclaimer, the term of this patent is extended or adjusted under 35 U.S.C. 154(b) by 165 days.

(21) Appl. No.: 12/680,806

(22) PCT Filed: Oct. 1, 2008

(86) PCT No.: PCT/US2008/078452

§ 371 (c)(1),
(2), (4) Date: Jun. 1, 2010

(87) PCT Pub. No.: WO2009/046110

PCT Pub. Date: Apr. 9, 2009

(65) Prior Publication Data

US 2010/0292348 A1   Nov. 18, 2010

Related U.S. Application Data

(60) Provisional application No. 60/976,774, filed on Oct. 1, 2007, provisional application No. 60/976,780, filed on Oct. 1, 2007.

(51) Int. Cl.
*C12Q 1/68* (2006.01)

(52) U.S. Cl.
USPC .................................. 435/6.1; 436/94

(58) Field of Classification Search
None
See application file for complete search history.

(56) References Cited

U.S. PATENT DOCUMENTS

| | | | |
|---|---|---|---|
| 5,637,716 A | 6/1997 | Komatsu et al. | |
| 5,897,945 A | 4/1999 | Lieber | |
| 6,036,774 A | 3/2000 | Lieber | |
| 6,528,020 B1 | 3/2003 | Dai | |
| 6,706,402 B2 | 3/2004 | Rueckes | |
| 6,709,566 B2 | 3/2004 | Cumings | |
| 6,716,620 B2 | 4/2004 | Bashir | |
| 6,723,299 B1 | 4/2004 | Chen | |
| 6,855,606 B2 | 2/2005 | Chen | |
| 6,914,279 B2 | 7/2005 | Lu | |
| 6,946,851 B2 | 9/2005 | Lee | |
| 7,105,428 B2 | 9/2006 | Pan | |
| 7,129,554 B2 | 10/2006 | Lieber | |
| 7,143,785 B2 | 12/2006 | Maerkl et al. | |
| 7,182,914 B2 | 2/2007 | Lai | |
| 7,256,466 B2 | 8/2007 | Lieber | |
| 7,301,199 B2 | 11/2007 | Lieber | |
| 7,303,875 B1 | 12/2007 | Bock | |
| 7,385,267 B2 | 6/2008 | Lieber | |
| 7,394,118 B2 | 7/2008 | Zhou | |
| 7,410,912 B2 | 8/2008 | Xu | |
| 7,416,911 B2 | 8/2008 | Heath | |
| 7,473,943 B2 | 1/2009 | Mostarshed | |
| 7,560,366 B1 | 7/2009 | Romano | |
| 7,619,290 B2 | 11/2009 | Lieber | |
| 7,632,234 B2 | 12/2009 | Manda | |
| 7,635,423 B2 | 12/2009 | Boussaad | |
| 7,662,652 B2 | 2/2010 | Zhou | |
| 7,670,831 B2 | 3/2010 | Lee | |
| 7,701,014 B2 | 4/2010 | Mostarshed | |
| 7,709,923 B2 | 5/2010 | Agarwal | |
| 7,718,995 B2 | 5/2010 | Kawashima | |
| 7,745,856 B2 | 6/2010 | Noy | |
| 7,785,922 B2 | 8/2010 | Robbins | |
| 7,795,677 B2 | 9/2010 | Bangsaruntip | |
| 2004/0018550 A1 | 1/2004 | Bellacosa | |
| 2004/0026684 A1 | 2/2004 | Empedocles | |
| 2004/0200734 A1 | 10/2004 | Co et al. | |
| 2004/0253741 A1 | 12/2004 | Star et al. | |
| 2005/0043894 A1* | 2/2005 | Fernandez | 702/19 |
| 2005/0065741 A1 | 3/2005 | Segal et al. | |
| 2005/0164236 A1* | 7/2005 | Su et al. | 435/6 |
| 2005/0250141 A1 | 11/2005 | Lambert et al. | |
| 2005/0253137 A1 | 11/2005 | Whang et al. | |
| 2005/0263798 A1 | 12/2005 | Kurth et al. | |
| 2006/0019319 A1 | 1/2006 | Billadeau et al. | |
| 2006/0035270 A1 | 2/2006 | Lee et al. | |
| 2006/0115640 A1 | 6/2006 | Yodh et al. | |
| 2006/0178841 A1 | 8/2006 | Fernandez | |
| 2006/0188934 A1* | 8/2006 | Chang et al. | 435/7.1 |

(Continued)

FOREIGN PATENT DOCUMENTS

CA    2701380    4/2009
CA    2701401    4/2009

(Continued)

OTHER PUBLICATIONS

Balog, Robert et al. Parallel assessment of CpG methyaltion by two color hybridization with oligonucleotide arrays. Analytical Biochemistry 2002 vol. 309 pp. 301-310.*
Li, Z et al. Sequence specific label free DNA sensors based on silicon nanowires. Nano Letters 2004 vol. 4 No. 2 pp. 245-247.*
Huang, et al. "Chemical sensors based on nanostructured materials," Sensors and Actuators B 122 (2007) 659-671.
Kim, et al. "The effect of metal cluster coatings on carbon nanotubes," Nanotechnology vol. 17, No. 2 (2006); abstract.
PCT/US08/78452 Written Opinion dated Dec. 24, 2008.
PCT/US08/78452 International Preliminary Report on Patentability dated Apr. 7, 2010.
PCT/US08/78491 International Search Report dated Mar. 23, 2009.
PCT/US08/78491 Written Opinion dated Mar. 23, 2009.
PCT/US08/78491 International Preliminary Report on Patentability dated Apr. 7, 2010.
PCT/US08/78502 International Search Report dated Jul. 23, 2009.
PCT/US08/78502 Written Opinion dated Jul. 23, 2009.
PCT/US08/78502 International Preliminary Report on Patentability dated Apr. 7, 2010.

(Continued)

*Primary Examiner* — James Martinell
(74) *Attorney, Agent, or Firm* — Seth D. Levy; Nixon Peabody LLP

(57) ABSTRACT

The present invention relates to various methods of detecting DNA methylation and defected DNA. In one embodiment, the invention provides a nanosensor bound to a probe that is complementary to a DNA methylation sequence.

8 Claims, 5 Drawing Sheets

(56) References Cited

U.S. PATENT DOCUMENTS

| | | |
|---|---|---|
| 2006/0240416 A1 | 10/2006 | Banerjee et al. |
| 2006/0292564 A1 | 12/2006 | Maier |
| 2007/0001581 A1 | 1/2007 | Stasiak et al. |
| 2007/0048181 A1 | 3/2007 | Chang et al. |
| 2007/0092870 A1 | 4/2007 | Zhao |
| 2007/0128744 A1 | 6/2007 | Tour et al. |
| 2007/0158766 A1 | 7/2007 | Lieber et al. |
| 2007/0161029 A1 | 7/2007 | Li et al. |
| 2007/0238186 A1 | 10/2007 | Sun |
| 2007/0264623 A1 | 11/2007 | Wang |
| 2008/0063587 A1 | 3/2008 | Strano et al. |
| 2008/0200342 A1 | 8/2008 | Rao et al. |
| 2008/0211040 A1 | 9/2008 | Lieber et al. |
| 2008/0280776 A1 | 11/2008 | Bashir |
| 2009/0027036 A1 | 1/2009 | Nuckolls et al. |
| 2009/0053743 A1 | 2/2009 | Link et al. |
| 2009/0110928 A1 | 4/2009 | Yukinobu |
| 2009/0124025 A1 | 5/2009 | Hamilton |
| 2009/0226927 A1 | 9/2009 | Sun |
| 2009/0246800 A1 | 10/2009 | Mattingly et al. |
| 2010/0112546 A1 | 5/2010 | Lieber |
| 2010/0152057 A1 | 6/2010 | Lieber |
| 2010/0204062 A1 | 8/2010 | Thompson |
| 2010/0256344 A1 | 10/2010 | Thompson |
| 2010/0260745 A1 | 10/2010 | Zhou et al. |
| 2011/0275544 A1 | 11/2011 | Zhou et al. |
| 2011/0287959 A1 | 11/2011 | Emerson et al. |

FOREIGN PATENT DOCUMENTS

| | | |
|---|---|---|
| CA | 2701447 | 7/2009 |
| CN | 102016570 A | 4/2011 |
| EP | 1312685 | 5/2003 |
| EP | 2205714 A0 | 7/2010 |
| EP | 2210093 | 7/2010 |
| JP | 2004-515782 A | 5/2004 |
| JP | 2006-505806 A | 2/2006 |
| JP | 2008-82988 A | 4/2008 |
| JP | 2012-163578 A | 8/2012 |
| WO | WO 2007/102629 A1 | 9/2007 |
| WO | 2008027078 | 3/2008 |
| WO | 2009046110 | 4/2009 |
| WO | 2009046136 | 4/2009 |
| WO | 2009085356 | 7/2009 |
| WO | 2010115143 | 10/2010 |
| WO | WO 2011/146881 A1 | 11/2011 |

OTHER PUBLICATIONS

CN Application No. 200880117550.4 Office Action dated Jan. 24, 2013.
CA Application No. 2,701,380 Examiner's Report dated Jan. 30, 2013.
CA Application No. 2,701,447 Examiner's Report dated Feb. 7, 2013.
U.S. Appl. No. 12/680,821 Non-Final Office Action dated Mar. 14, 2013.
CA Application No. 2,701,380 Examiner's Report dated Apr. 12, 2012.
CA Application No. 2,701,401 Examiner's Report dated Jan. 30, 2012.
EP Application No. 08835597.9 Examination Report dated Mar. 21, 2012.
EP Application No. 08867520.2 Extended Search Report dated Nov. 6, 2012.
JP Application No. 2010-528111 Official Action dated Jan. 5, 2012.
U.S. Appl. No. 12/680,821 Restriction Requirement dated Aug. 9, 2012.
U.S. Appl. No. 12/680,833 Restriction Requirement dated Aug. 7, 2012.
U.S. Appl. No. 12/614,239 Restriction Requirement dated Apr. 11, 2012.
U.S. Appl. No. 12/614,239 Non-Final Office Action dated Jul. 9, 2012.
U.S. Appl. No. 12/753,688 Restriction Requirement dated May 7, 2012.
U.S. Appl. No. 12/753,688 Non-Final Office Action dated Nov. 29, 2012.
U.S. Appl. No. 13/112,754 Restriction Requirement dated Aug. 1, 2012.
PCT/US2010/029837 International Preliminary Report on Patentability dated Oct. 4, 2011.
PCT/US2010/029837 Written Opinion dated Jun. 9, 2011.
PCT/US2010/029837 International Search Report dated Jun. 9, 2011.
PCT/US2011/037408 International Search Report dated Aug. 19, 2011.
PCT/US2011/037408 Written Opinion dated Aug. 19, 2011.
PCT/US2011/037408 International Preliminary Report on Patentability dated Nov. 20, 2012.
Balog et al. Parallel assessment of CpG methylation by two-color hybridization with oligonucleotide arrays. Analytical Biochemistry. (2002). 309:301-310.
Li et al. Sequence-Specific Label-Free DNA Sensors based on Silicon Nanowires. Nano Letter. (2004). 4(2):245-247.
Li et al. Complimentary Detection of Prostate-Specific Antigen Using $In_2O_3$ Nanowires and Carbon Nanotubes. J. Am. Chem. Soc. (2005). 127(36):12484-12485.
Livnah et al. Three-dimensional structures of avidin and the avidin-biotin complex. PNAS (1993). 90:5076-5080.
Patolsky et al. Nanowire-Based. Analytical Chemistry (2006). 78(13):4261-4269.
Ranki et al. Sandwich hybridization as a convenient method for the detection of nucleic acids in crude samples. Gene. (1983). 77-85.
Star et al. Label-free detection of DNA hybridization using carbon nanotube network field-effect transistors. PNAS (2006). 103(4):921-926.
EP Application No. 08835597.9 Examination Report dated Jan. 25, 2013.
U.S. Appl. No. 13/112,754 Non-Final Office Action dated Mar. 21, 2013.
Kartalov et al. High-throughput multi-antigen microfluidic fluorescence immunoassays. BioTechniques (2006). 40 (1): 85-90.

\* cited by examiner

SEQUENCE LISTING

```
<160> NUMBER OF SEQ ID NOS: 16

<210> SEQ ID NO 1
<211> LENGTH: 25
<212> TYPE: DNA
<213> ORGANISM: Homo sapiens

<400> SEQUENCE: 1
tggggcggat cgagtgcgtt cggcg                                         25

<210> SEQ ID NO 2
<211> LENGTH: 25
<212> TYPE: DNA
<213> ORGANISM: Homo sapiens

<400> SEQUENCE: 2
cgccgaacgc actcgatccg cccca                                         25

<210> SEQ ID NO 3
<211> LENGTH: 25
<212> TYPE: DNA
<213> ORGANISM: Homo sapiens

<400> SEQUENCE: 3
tggggtggat tgagtgtgtt tggtg                                         25

<210> SEQ ID NO 4
<211> LENGTH: 25
<212> TYPE: DNA
<213> ORGANISM: Homo sapiens

<400> SEQUENCE: 4
caccaaacac actcaatcca cccca                                         25

<210> SEQ ID NO 5
<211> LENGTH: 25
<212> TYPE: DNA
<213> ORGANISM: Homo sapiens

<400> SEQUENCE: 5
tggggcggat cgagtgcgtt cggcg                                         25
```

-continued

<210> SEQ ID NO 6
<211> LENGTH: 25
<212> TYPE: DNA
<213> ORGANISM: Homo sapiens

<400> SEQUENCE: 6
cgccgaacgc actcgatccg cccca                                              25

<210> SEQ ID NO 7
<211> LENGTH: 25
<212> TYPE: DNA
<213> ORGANISM: Homo sapiens

<400> SEQUENCE: 7
cgccgaatgc acttgatctg cccca                                              25

<210> SEQ ID NO 8
<211> LENGTH: 25
<212> TYPE: DNA
<213> ORGANISM: Homo sapiens

<400> SEQUENCE: 8
cgccgaacgc acttgatctg cccca                                              25

<210> SEQ ID NO 9
<211> LENGTH: 25
<212> TYPE: DNA
<213> ORGANISM: Homo sapiens

<400> SEQUENCE: 9
cgccgaatgc actcgatctg cccca                                              25

<210> SEQ ID NO 10
<211> LENGTH: 25
<212> TYPE: DNA
<213> ORGANISM: Homo sapiens

<400> SEQUENCE: 10
cgccgaatgc acttgatccg cccca                                              25

<210> SEQ ID NO 11
<211> LENGTH: 25
<212> TYPE: DNA
<213> ORGANISM: Homo sapiens

<400> SEQUENCE: 11
cgccgaacgc actcgatctg cccca                                              25

<210> SEQ ID NO 12
<211> LENGTH: 25
<212> TYPE: DNA
<213> ORGANISM: Homo sapiens

<400> SEQUENCE: 12
cgccgaacgc acttgatccg cccca                                              25

<210> SEQ ID NO 13
<211> LENGTH: 25
<212> TYPE: DNA
<213> ORGANISM: Homo sapiens

<400> SEQUENCE: 13
cgccgaatgc actcgatccg cccca                                              25

```
<210> SEQ ID NO 14
<211> LENGTH: 23
<212> TYPE: DNA
<213> ORGANISM: Homo sapiens

<400> SEQUENCE: 14
ggaggggttg gttggttatt aga                                              23

<210> SEQ ID NO 15
<211> LENGTH: 20
<212> TYPE: DNA
<213> ORGANISM: Homo sapiens

<400> SEQUENCE: 15
aaaactccat actactcccc                                                  20

<210> SEQ ID NO 16
<211> LENGTH: 12
<212> TYPE: DNA
<213> ORGANISM: Homo sapiens

<400> SEQUENCE: 16
ttagagggtg gg                                                          12
```

DETECTION OF METHYLATED DNA AND DNA MUTATIONS

CROSS-REFERENCE TO RELATED APPLICATIONS

This application is the National Phase of International Application PCT/US08/78452, filed Oct. 1, 2008, which designated the U.S. and that International Application was published under PCT Article 21(2) in English. This application also includes a claim of priority under 35 U.S.C. §119(e) to U.S. provisional patent application No. 60/976,774, filed Oct. 1, 2007 and U.S. provisional patent application No. 60/976,780, filed Oct. 1, 2007.

FIELD OF THE INVENTION

The invention relates to the field of biotechnology; specifically, to detection of methylated DNA and DNA mutation.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The field of epigenetics has lagged behind genetics due to the lack of robust assays to measure DNA methylation. DNA methylation sensitive restriction enzymes were used in the first attempts to interrogate specific CpG sites for methylation. The use of methylation sensitive enzymes with Southern blotting or PCR (polymerase chain reaction) allowed the investigation of a limited number of individual CpG sites that were targets of restriction enzymes. The field of epigenetics was improved by the advent of DNA methylation using bisulfite treatment. This induces a primary sequence change in the DNA based on the DNA methylation status. Unmethylated C is converted to U and then to T by subsequent PCR. 5 mC remains unchanged and is read as C by subsequent PCR amplification.

This sequence can be assessed by a number of different methods: direct Sanger sequencing (bisulfite sequencing), restriction digests (COBRA), methylated-sequence specific PCR (MSP), sequence specific real time PCR (MethyLight/quantitative MSP), nucleotide extension assays (MS-SNuPE), and Pyrosequencing. However, these methods are labor intensive and do not lend themselves to high throughput assays. Currently, array based methods to measure DNA methylation of more than one gene do exist, but these depend upon multiplex bisulfite-PCR or restriction digestion with methylation sensitive restriction enzymes.

Thus, there is a need in the art for systems and methods to detect DNA methylation and mutations that do not require the use of PCR or other DNA amplification procedures.

SUMMARY OF THE INVENTION

Various embodiments provide methods of preparing a nanosensor to detect DNA methylation, comprising providing a nanosensor, and attaching a probe to the nanosensor, where the probe is adapted to bind a methylated DNA sequence. In another embodiment, the nanosensor comprises nanotube and nanowire surfaces. In another embodiment, the nanosensor is an NW/NT sensor. In another embodiment, the probe comprises a polynucleotide. In another embodiment, the probe is adapted to bind an agent. In another embodiment, the agent comprises a signal amplifier. In another embodiment, the probe comprises SEQ. ID. NO.: 1, SEQ. ID. NO.: 2, SEQ. ID. NO.: 3, SEQ. ID. NO.: 4, or a combination thereof. In another embodiment, the probe may comprise SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, or a combination thereof.

Other embodiments provide a nanosensor for detecting defected DNA, comprising a NW/NT sensor, and a probe bound thereto, where the probe is adapted to bind to a defected DNA. In another embodiment, the probe is a polynucleotide. In another embodiment, the polynucleotide comprises a CG rich sequence. In another embodiment, the defected DNA comprises a methylated nucleotide. In another embodiment, the defected DNA comprises a point mutation. In another embodiment, the probe and defected DNA are adapted to bind as complementary polynucleotides.

Other embodiments provide a method of detecting a defected nucleotide in a DNA sample, comprising providing a nanosensor configured to detectably change when a defected nucleotide bound to a probe on the nanosensor is itself bound by an agent, contacting the nanosensor with a sample, and contacting the nanosensor with the agent, where the nanosensor detectably changes if the sample comprises the defected nucleotide. In another embodiment, the agent comprises a methyl-CpG binding protein. In another embodiment, the agent comprises MBD1, MBD2, MBD4 and/or MeCP272. In another embodiment, the agent comprises an antibody. In another embodiment, the defected nucleotide comprises a point mutation. In another embodiment, the agent comprises a DNA repair protein. In another embodiment, the defected nucleotide comprises a methylated DNA nucleotide.

Various embodiments also provide a method of diagnosing a disease in an individual in which the presence or absence of methylation for a plurality of genetic loci is associated with the disease, comprising using a nanosensor to determine the presence or absence in the individual of the methylation in the plurality of genetic loci, and diagnosing the individual as having the disease if the individual demonstrates the presence or absence of the methylation of the plurality of genetic loci. In another embodiment, the disease is cancer.

Other embodiments provide a method of treating a disease in an individual in which the presence or absence of methylation for a plurality of genetic loci is associated with the disease, comprising using a nanosensor to determine the presence or absence in the individual of the methylation in the plurality of genetic loci, diagnosing the individual as having the disease if the individual demonstrates the presence or absence of the methylation of the plurality of genetic loci, and treating the disease, if the individual is diagnosed as having it. In another embodiment, the disease is cancer.

Other features and advantages of the invention will become apparent from the following detailed description, taken in conjunction with the accompanying drawings, which illustrate, by way of example, various embodiments of the invention.

BRIEF DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

Figure 1:
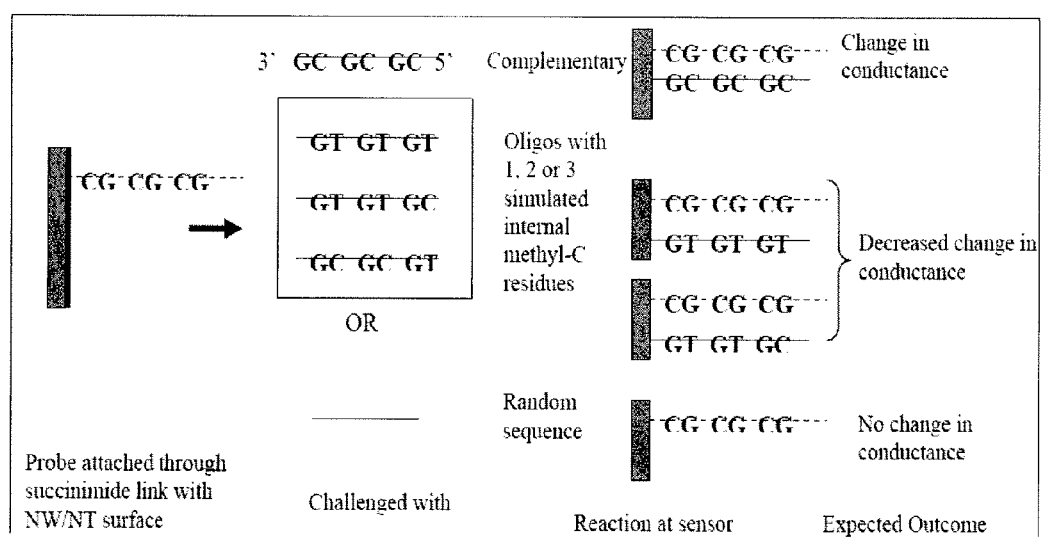
FIG. 1 depicts, in accordance with an embodiment described herein, a design for detecting simulated methylation status using NW/NT sensors.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, "MBP" means methyl binding protein. There are various methyl binding proteins that may be used in accordance with various embodiments described herein, and include but are not limited to, MBD1, MBD2, MBD4, MeCP272 and the Kaison protein family.

As used herein, "MBD" means methyl-CpG-binding domain.

As used herein, "NW/NT FET sensor" refers to a novel nanowire/nanotube field effect transistor sensor. Similarly, "NW/SWNT FET sensor" refers to a novel nanowire/single-walled carbon nanotube field effect transistor sensor.

As used herein, a "CG" rich polynucleotide sequence is a nucleotide sequence made up of a large amount of cytosine and guanine.

As used herein, "MMR" refers to mismatch repair protein.

Oligonucleotides may be used, in conjunction with various embodiments described herein, to detect methylation of a gene. For example, oligonucleotides M-p16, M-p16-Comp, U-p16 and U-p16-Comp may be used to detect methylation of a p16 gene. Examples of oligonucleotides M-p16, M-p16-Comp, U-p16 and U-p16-Comp, are described herein as SEQ. ID. NO.: 1, SEQ. ID. NO.: 2, SEQ. ID. NO.: 3, and SEQ. ID. NO.: 4, respectively. Similarly, in conjunction with various embodiments described herein, combinations of methylation sites may be used to quantitate DNA methylation of specific sites. For example, sequence of the probe attached on NW/NT surface, fully methylated probe, fully unmethylated probe, partial methylated probe—site 1, partial methylated probe—site 2, partial methylated probe—site 3, partial methylated probe—site 1,2, partial methylated probe—site 1,3, and partial methylated probe—site 2,3 are described herein as SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. D. NO.: 12, and SEQ. ID. NO.: 13, respectively.

In conjunction with various embodiments described herein, it may be desirable to use bisulfite PCR for p16 gene to assess DNA methylation. As used herein, an example of forward primer, a biotinylated reverse primer, and a sequencing primer, are described as SEQ. ID. NO.: 14, SEQ. ID. NO. 15, and SEQ. ID. NO.: 16, respectively.

Figure 2:
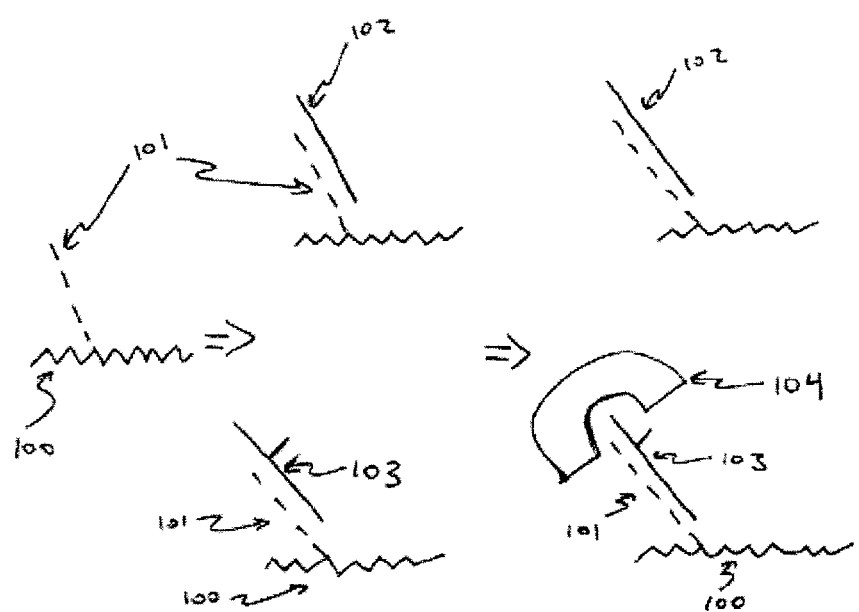
FIG. 2 depicts, in accordance with an embodiment described herein, a schema of NT/NW sensor array using methyl-CpG-binding protein (clone MBD2) to detect DNA methylation (CH3). Complementary DNA or target sequence 102 will hybridize to the probe 101 bound to NW/NT 100. MCB 104 will be added, and will specifically bind to methylated DNA 103, but not non-methylated DNA 102. It is expected that the MBD-binding will change in conductance in a measurable way.
Figure 3:
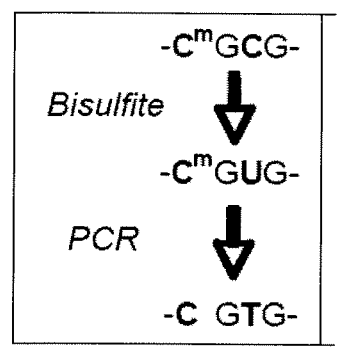
FIG. 3 (prior art) depicts a schematic demonstrating biosulfite treatment of DNA converts cytosine, but not methylated cytosine, to uracil. During subsequent PCT, uracil is converted to thymine and methylated cytosine is still recognized as cytosine and unmethylated DNA is converted to thymine.

As disclosed herein, the inventors developed a quantitative method for measuring gene-specific DNA methylation that requires neither bisulfite treatment of DNA nor PCR (an example of a bisulfite treatment and PCR reaction for measuring DNA methylation is depicted herein as FIG. 3). As depicted in FIG. 1 and FIG. 2, DNA may be denatured, endonuclease-restricted and directly hybridized to a nanowire-single-walled carbon nanotube field effect transistor (NW/SWNT FET sensors). Methyl-CpG Binding Protein may then be used to bind specifically to methylated DNA that has hybridized to the NW/SWNT FET sensor device. The binding will directly change the conductance characteristics of the NW/SWNT FET, thus identifying methylated sequences. The signal can also be enhanced by binding signal enhancers directly to the Methyl-CpG Binding Protein. The detection method may also be extended to any defected DNA, including sequences with an altered based, where DNA repair proteins that have a component that binds selectively to mismatched regions of duplex DNA may be used in a manner similar to the Methyl-CpG Binding Protein. Additionally, the nanobiosensor may also be used in conjunction with a microfluidic device.

Figure 4:
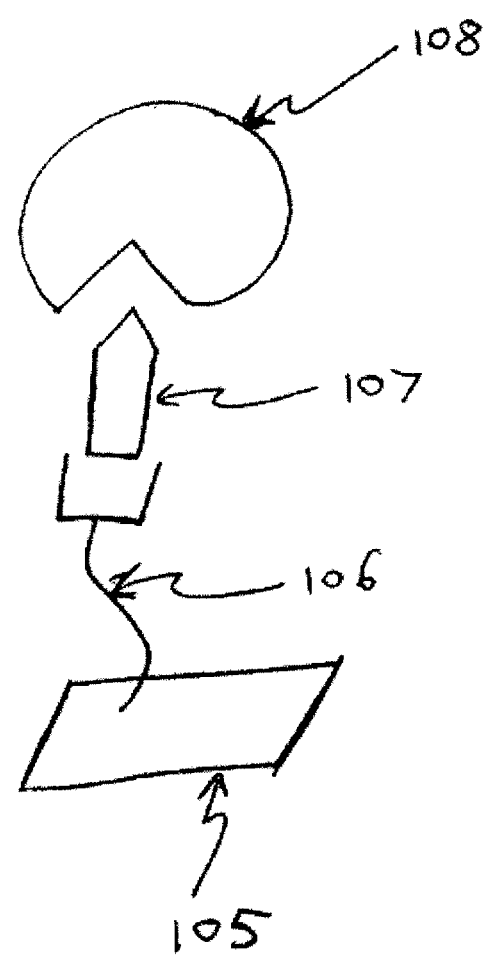
FIG. 4 depicts, in accordance with an embodiment described herein, a nanosensor 105 attached to a probe 106 configured to bind a target 107, where there is a change in conductance when the probe 106 binds to the target 107. In accordance with another embodiment described herein, there is a change in conductance when an agent 108 interacts with the target 107 and/or probe 106.

In one embodiment, a nanosensor 105 is attached to a probe 106 configured to bind a target 107, where there is a change in conductance when the probe 106 binds to the target 107. In another embodiment, there is a change in conductance when an agent 108 interacts with the target 107 and/or probe 106. An example is provided herein as FIG. 4.

In one embodiment, the present invention provides a method of direct detection of methylated polynucleotides by the following steps, or combinations thereof: (1) a probe is bound to a nanosensor; (2) a methylated target sequence complementary to the probe is hybridized to the probe; and (3) a Methyl-CpG Binding Protein binds to the methylated target sequence, thereby enabling direct detection of methylated polynucleotides. In another embodiment, the binding of the Methyl-CpG Binding Protein results in a detectable change in conductance of the nanosensor. In another embodiment, the Methyl-CpG Binding Protein is MBD1, MBD2, MBD4, MeCP272, a Kaison protein, and/or an engineered methyl binding protein. In another embodiment, the engineered methyl binding protein is genetically engineered methyl binding protein (4×MBD).

Figure 5:
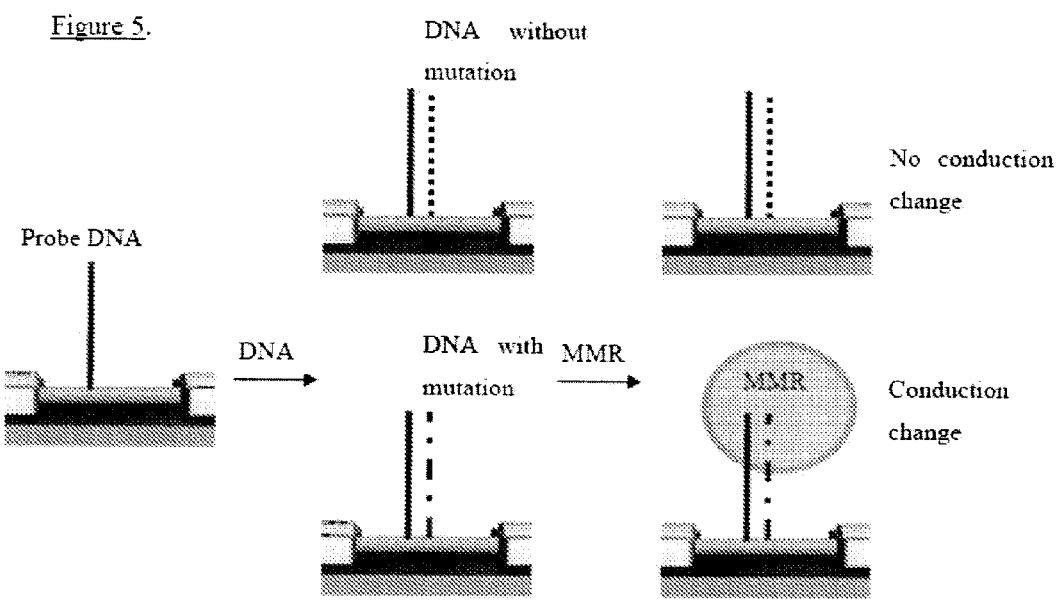
FIG. 5 depicts, in accordance with an embodiment described herein, a mutation detection scheme. First, NW/CNT devices are functionalized with probe DNAs complementary to the target DNA sequence. The devices are then exposed to the solution under analysis. Complementary DNAs to the probe DNA, regardless of the existence of mutation, will be captured by the probe DNA if it exists in the solution. However, addition of mutation detection protein will differentiate DNA hybrids with and without mutation, thus generate signal only from a device where the DNA hybrids have point mutation. Another advantage of using the mutation detection protein is that it carries larger charges than DNAs, which will result in an enhanced signal.

In another embodiment, an example depicted by FIG. 5, the present invention provides a method of detecting a mutation in a polynucleotide by the following steps, or combinations thereof: (1) a probe is bound to a nanosensor, where the probe is adapted to bind to a targeted mutation sequence; (2) a targeted mutation sequence binds to the probe; and (3) a DNA repair protein binds to the targeted mutation sequence, thereby enabling the detection of the targeted mutation sequence. In another embodiment, the binding of the DNA repair protein to the targeted mutation sequence results in a detectable change in conductance of the nanosensor.

In another embodiment, the present invention provides a nanosensor for detecting defected DNA comprising a nanosensor bound to a probe adapted to bind a target sequence, wherein the nanosensor can detect when an agent binds the target sequence. In another embodiment, the defected DNA is a methylated DNA. In another embodiment, the agent is a methyl binding protein. In another embodiment, the agent is an antibody. In another embodiment, the agent is a DNA repair protein.

In another embodiment, the present invention provides an apparatus for detecting and/or monitoring a disease and/or condition comprising a nanosensor bound to a plurality of capture molecules, wherein the plurality of capture molecules may recognize a molecular signature associated with a disease and/or condition. In another embodiment, the nanosensor includes a NW/NT FET sensor and/or NW/SWNT FET sensor. In another embodiment, the capture molecule may be a polynucleotide, polypeptide, antibody, aptamer, receptor, ligand, or combinations thereof. In another embodiment, the disease and/or condition is cancer.

In another embodiment, the present invention provides a method of treating a disease and/or condition by determining the presence of a molecular signature associated with a disease and/or condition, and treating the disease and/or condition.

The present invention is also directed to a kit to detect DNA methylation or mutations. The kit is an assemblage of materials or components, including at least one of the inventive compositions. Thus, in some embodiments the kit contains a composition including probes, target sequences and agents that may bind the target sequences, as well as nanowire and nanotube and nanosensor components as described above.

The exact nature of the components configured in the inventive kit depends on its intended purpose. For example, some embodiments are configured for the purpose of detecting DNA methylation. In another embodiment, the kit is configured particularly for the purpose of detecting defected DNA and/or mutations. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to detect DNA methylation. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing probes, targeting sequences, and binding proteins. The packaging material generally has an external label which indicates the contents and/or purpose of the kit and/or its components.

EXAMPLES

The following example is provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

The inventors have developed methods of using nanowire or nanotube based sensors for the direct detection of methylated DNA nucleotides without the aid of a bisulfite treatment and PCR amplification. Currently, DNA methylation detection technologies require bisulfite treatment and prior PCR amplification. The inventors have developed a technique that eliminates this preprocessing step and thus allows for the development of a cost-effective "lab-on-chip" assay.

Example 2

Methylation Detection Via Methyl-Binding Protein and Antibodies

Proteins that specifically bind methylated DNA can also identify DNA methylation. Antibodies have been developed that specifically bind methylated but not unmethylated DNA. This antibody has been previously useful for in vitro studies that map 5 mC distribution in the genome. Alternatively there are naturally occurring DNA methylation binding proteins that bind specifically to methylated DNA. There are two families of enzymes that bind DNA methylation in mammals. The first are methyl-binding proteins (MBP) that contain the methyl-CpG-binding domain (MBD). The members of this protein family include MBD1, MBD2, MBD4 and MeCP272. The second is the Kaison protein family that also binds CpG methylation. All of these proteins have been shown to repress transcription in vitro. The inventors have developed a novel method of detecting DNA methylation via interaction of methylated cytosine in DNA with methyl binding protein.

Example 3

Comparing the Nanosensing Assay for Detection of DNA Methylation

Several specific methods have been developed to detect site-specific methylation. Pyrosequencing is an example of one that is accurate and reliable and it can be a method against which a nanosensing assay may be compared. NW/SWNT FET technology described herein may be compared to bisulfite-PCR pyrosequencing.

Example 4

Direct Detection of Methylated DNA

The inventors also used an NW/NT FET sensor to detect assay bisulfite treated DNA, as well as used Methyl-CpG Binding Protein along with NW/SWNT FET sensor arrays to detect methylated DNA sequences without the need for bisulfite. This novel approach allows detection and quantitation of DNA methylation without the need for bisulfite treatment of DNA and the need for PCR. The inventors also may employ NW/NT FET sensor array that can allow many advantages over existing technologies for detecting DNA methylation. These advantages can include the potential for simultaneous detection of methylation for multiple genes in an array format, allowing a combination of sensitivity, speed and scale to detect DNA methylation not provided by existing formats.

Example 5

Methyl-Binding Protein

The genes encoding MBD1, MBD2, MBD3 and MBD4 have been cloned into pET6H expression vector. The MBD1, MBD2, MBD3 and MBD4 have been previously described (Hendrich, et al, Mol Cell Biol, 1998 November; 18(11): 6538-47). MBD1, MBD2 and MBD4 have been shown to bind methylated DNA in vitro independent of sequence context. All enzymes show a preference for symmetrically methylated DNA, however MBD1 and MBD4 also can bind hemimethylated DNA. A genetically engineered poly-MBD has been developed from MBD1. This genetically engineered protein was manufactured by multimerizing the methyl binding protein of MBD1. This engineered methyl-CpG-binding protein (4×MBD) has a 55-fold binding affinity to a single methylated CpG site than wild-type MBD1 (1×MBD). 4×MBD has an 81 fold higher binding affinity for target DNA that has 3 methylated CpG sites compared to 1×MBD. (Table 1.) This engineered MBD may be used with the NW/SWNT FET array to detect methylated DNA using a protein marker.

Example 6

Table 1

Binding Constants for a Cloned Methyl Binding Domain (1×MBD) Versus an Engineered Methyl Binding Protein that is 4 Multimerized MBD (4×MBD) (Jorgensen et al, Nucleic Acids Research 2006 Aug. 7; 34(13): e96)

TABLE 1

| Methyl CpG Binding Protein | 1 methyl CpG | 2 methyl CpG's | 3 methyl CpG's |
| --- | --- | --- | --- |
| 4×MBD | 0.5 uM | 0.05 Um | 0.02 uM |
| 1×MBD | 30 uM | 3 uM | 2 uM |
| 4x/1x ratio | 55 | 59 | 81 |

Example 7

Detection of Methylated DNA Via Targeted Hybridization of the Sequence of Interest Using Indium Oxide Nanowire and Carbon Nanotube Sensor p16 gene methylation in defined sequences are analyzed. Bisulfite reaction typically results in conversion of unmethylated C to T, while the methylated C is unaffected; this is then followed by PCR. The inventors target specific detection of simulated methyl-C residues using NW/SWNT BET sensors. The inventors will use the NW/SWNT BET sensors with known concentrations of synthetic oligonucleotides with a sequence designed to simulate the routine bisulfite-mediated conversion of methyl and non-methyl C, followed by use in cell lines with varying degrees of methylation in the p16 gene known to be biologically relevant. NW/SWNT BET sensors may be functionalized using oligonucleotides directed to the p16 gene sequence simulated to reflect bisulfite conversion. The initial ligands on nanowire and nanotube surfaces will consist of two oligonucleotide pairs that will be directed to either fully methylated or unmethylated p16 gene sequences. (Table 2) NW/SWNT NET sensors may be tested for hybridization between the probes and their respective complementary oligonucleotide sequences as positive controls (i.e. M-p16 and Mp16 Comp, or U-p16 and U-p16 Comp). As a negative control, the corresponding M-U oligonucleotides may be used (i.e. M-p16 and U-p16). In addition, diluted standards of M and U oligonucleotides may be used to calibrate the NW/SWNT BET sensors, and determine the ability of the NW/SWNT BET sensors to quantitate p16 DNA methylation, in an oligonucleotide mock standard.

Example 8

Table 2

Oligonucleotides to be Used with the NT/NW Sensor Array to Detect Methylation of the p16 Gene

TABLE 2

| Oligonucleotide Name | Target | Sequence |
| --- | --- | --- |
| M-p16 | Methylated p16 | SEQ. ID. NO.: 1 |
| M-p16-Comp | Methylated p16 | SEQ. ID. NO.: 2 |
| U-p16 | Unmethylated p16 | SEQ. ID. NO.: 3 |
| U-p16-Comp | Unmethylated p16 | SEQ. ID. NO.: 4 |

Example 9

Detection of Variable Internal Cytosine Methylations in Oligonucleotides of Using Indium Oxide Nanowires and Carbon Nanotubes The ability of the inventors' NW/SWNT FET sensor array to distinguish different patterns of partial DNA methylation will be determined by using oligonucletides with different combinations of C/T. The M-p16 oligonucleotide (SEQ. ID. NO.: 1) will be hybridized to a series of oligonucleotides based on the M-p16-Comp oligonucleotide (SEQ. ID. NO.: 2), where Y represents either C or T, in order to simulate methylated or unmethylated sites. Methylation of all three sites within the oligonucleotide may be tested (ie. C-T-T, T-C-T, and T-T-C). This represents one of the three CpG sites being methylated. In addition combinations of may be tested to simulate 2 of 3 sites being methylated (ie. C-C-T, C-T-C, and T-C-C). The use of these oligonucletides will simulate "partial" DNA methylation, and will test the ability of the NW/SWNT FET sensor array to quantitate the DNA methylation of specific CpG sites, and determine which CpG site is methylated within a target region. (FIG. 1 and Table 3).

Example 10

Table 3

Probe and Target Sequences for Detection of Simulated Methylation

TABLE 3

| | |
| --- | --- |
| Sequence of the Probe attached on NW/NT surface | SEQ. ID. NO.: 5 |
| INCOMING TARGET | SEQUENCE |
| Fully Methylated (C-C-C) Probe | SEQ. ID. NO.: 6 |
| Fully Unmethylated Probe | SEQ. ID. NO.: 7 |
| Partial Methylated Probe (C-T-T)-Site 1 | SEQ. ID. NO.: 8 |
| Partial Methylated Probe (T-C-T)-Site 2 | SEQ. ID. NO.: 9 |
| Partial Methylated Probe (T-T-C)-Site 3 | SEQ. ID. NO.: 10 |
| Partial Methylated Probe (C-C-T)-Site 1, 2 | SEQ. ID. NO.: 11 |
| Partial Methylated Probe (C-T-C)-Site 1, 3 | SEQ. ID. NO.: 12 |
| Partial Methylated Probe (T-C-C)-Site 2, 3 | SEQ. ID. NO.: 13 |

Example 11

Direct Detection of Methylated DNA Via Methylation Binding Proteins

A NW/SWNT FET sensor array functionalized with an oligonucleotide complementary to the p16 gene promoter may be manufactured as described herein and used in conjunction with a protein that specifically binds methylated but not unmethylated DNA. The use of this methyl-CpG binding protein will be used in lieu of bisulfite treatment and PCR to detect DNA methylation. A second sensor array functionalized with a non-specific oligonucleotide may also be manufactured to serve as a negative control. Methyl-CpG binding protein may also be manufactured where recombinant proteins will be expressed in *E. coli* using cloned pET6H expression vector, and purified by loading onto a nickel agarose column (Qiagen Fractogel EMD (Merck Inc., USA). During development all combinations of NW/SWNT FET sensor array with a methylated oligonucleotide and unmethylated oligonucleotide may be tested. In addition, each methyl-CpG binding protein may be tested with each NW/SWNT FET sensor array combination. A newly engineered high affinity methyl-CpG binding protein may also be employed with the NW/SWNT FET sensor array. A genetically engineered poly-MBD protein from MBD1 may be manufactured by multimerizing the methyl binding protein of MBD1. This engineered methyl-CpG-binding protein has a >50-fold binding affinity to methylated DNA than wild-type MBD1. This engineered MBD may also be used with the NW/SWNT FET array to detect methylated DNA using a protein marker. DNA of interest may be denatured and hybridized to p16 sequence specific oligonucleotides affixed to the NW/SWNT FET sensor. High molecular weight DNA will be sheared with sonication or digested with a restriction enzyme to reduce the target molecule size. Both methods may be employed initially to determine which is optimal to allow hybridization of a denatured DNA to hybridize to the sensor array.

Example 12

Adding Methyl-CpG Binding Protein to the Array

Methyl-CpG binding protein may be added to the array to specifically bind methylated DNA and trigger a signal in the sensor array. The methyl-CpG binding protein will be hybridized to the target DNA hybridized to the NW/SWNT FET sensor array. The binding protein may be hybridized in 20 mM HEPES, ph 7.9, 10% glycerol and 1 mM DTT, conditions that have shown good binding of methyl CpG binding protein in previous gel shift assays. MBP-based detection may be tested at a variety of concentrations to find the optimal concentration of MBP protein with the highest signal to noise ratio for detection of methylated DNA using NW and NT sensors. Unmethylated DNA will also hybridize to the NW/SWNT FET sensor array, but will not interact with the methyl-CpG binding protein.

Example 13

DNA Methylation may Function as a Clinical Biomarker

The ability to simultaneously detect methylation for multiple genes in an array format allows a combination of sensitivity, speed and scale to detect DNA methylation not provided by existing formats. DNA methylation is the postreplicative chemical modification of DNA. Cytosine can be methylated to 5-methylcytosine at the palindromic CpG dinucleotide. DNA methylation is associated with transcriptional silencing of genes. Aberrant DNA methylation is a common finding in all cancers. Hypermethylation of normally unmethylated CpG rich areas referred to CpG islands seems to be the most prevalent event described in cancer. Methylation of CpG islands associated with the promoter region of genes leads to the aberrant silencing of numerous genes including a number of tumor suppressor genes. The list of genes that have been found to be hypermethylated in cancer is now exhaustive. MLH1, ARF, p16, APC, CDH1, DAPK1, GSTP1, and p15 are often studied as biomarkers for early cancer detection. However, in the past, methods employed to detect aberrant DNA methylation of these genes are dependent on bisulfate-PCR technology. Therefore the same assay can be adapted to any gene or genome locus by selecting the appropriate PCR primers. These DNA methylation markers have been used successfully to classify different cancers, and characterize certain phenotypes. There are numerous reports that describe the hypermethylation of a gene being associated with prognosis for gastric, lung, esophageal, pancreatic and colon cancer. Acute lymphoblastic leukemia and acute myeloid leukemia with hypermethylation have also been associated with a poorer outcome. DNA methylation patterns have also been shown to predict response or resistance to therapy in glioma and melanoma. The inventors optimized their technology by using the p16 gene. The p16 gene is a tumor suppressor gene involved in numerous types of cancer. The p16 protein plays a key role in controlling the cell cycle by inhibiting the cyclin-dependent kinase 4 and preventing the phosphorylation of retinoblastoma protein. The p16 gene can be inactivated by either mutation or deletion of chromosome 9p. However, it appears that the p16 promoter, which is a CpG island, can be frequently inactivated by hypermethylation in cancer.

Example 14

Cell Line and Culture Conditions for Methylation Sensing

Three cancer cell lines: RKO (Colon), Hct116 (Colon), and HepG2 may be used to assess DNA methylation. The inventors have previously found that these cell lines have varying amounts of p16 gene methylation. RKO is heavily (94%), Hct116 is intermediate (37%), and HepG2 has low levels of p16 methylation (<2%). The use of three different cell lines with distinct levels of DNA methylation allow the inventors to validate the assay system. Cells may be cultured in DMEM with 10% fetal bovine serum. DNA will be extracted. Then DNA from these cell lines will be separately quantitated by standard bisulfite-PCR Pyrosequencing or by NW/SWNT FET sensors. Bisulfite conversion of DNA to assess DNA methylation may be performed, where bisulfite PCR for p16 gene may be performed using the forward primer (SEQ. ID. NO.: 14), a biotinylated reverse primer (SEQ. ID. NO.: 15), and a sequencing primer (SEQ. ID. NO.: 16).

For nanosensing experiments, the DNA isolated from cell lines may be digested with the restriction enzymes, PfimI and NgomIV, to create a target p16 sequence of 76 base pairs in size. The DNA may then be denatured by heating to 95° C. or mild alkali treatment prior to hybridization to the NW/SWNT FET sensor array. For hybridization to the NW/SWNT FET array, it may be functionalized with about 75 nucleotide synthetic sequence complementary to incoming target DNA. These assays can test the ability of nanosensors to differentiate between differential hybridization of incoming DNA to probe DNA based on the levels of methylation in a group of samples where DNA methylation has been previously measured by Pyrosequencing.

Example 15

DNA Mutation Detection

The NW/CNT devices are functionalized with probe DNAs complementary to the target DNA sequence. The devices are then exposed to the solution under analysis. Complementary DNAs to the probe DNA, regardless of the existence of mutation, will be captured by the probe DNA if it exists in the solution. However, addition of mutation detection protein will differentiate DNA hybrids with and without mutation, thus generating a signal only from a device where the DNA hybrids have point mutation. Another advantage of using mutation detection protein is that it carries larger charges than DNAs, which will result in an enhanced signal.

Example 16

DNA Mutation Detection

Materials and Methods

For device preparation, NW/CNT devices were fabricated with probe DNAs attached to the NW/CNT surface by using appropriate linker molecules. Amine terminated probe DNAs, which are commercially available, may be used to form amide bond between the linker and probe DNAs. Mutation binding protein may be purchased from a vendor or produced using various methods readily known to those of skill in the art.

Example 17

DNA Mutation Detection

Sensing Experiments

The schematic diagram of the measurement setup is shown in FIG. 5 herein. A chemical cell made of teflon was mounted onto the device, and filled with phosphate saline buffer (PBS). A Pt wire was inserted into the buffer, and served as a gate electrode (liquid gate). This liquid gate can be used to tune the sensitivity of devices. Solutions of interest will be added to the buffer, and the conductance through the device will be monitored.

Example 18

Making Nanosensors

Nanotube Fabrication

The inventors have fabricated carbon nanotube FET arrays in a multistep process, comprising:
(1) Catalyst preparation: Quartz substrates were photolithographically patterned to make openings for catalysts. A solution of ferritin (Sigma) in de-ionized (D.I.) water was dropped onto the substrates, and kept for 10 min. The substrates were then rinsed with D.I. water, and the photoresist layer was lifted off in acetone. The substrate with ferritin particles was calcinated at 700° C. for 10 min to form iron oxide nanoparticles that act as catalysts.
(2) Aligned carbon nanotube growth: A chemical vapor deposition (CVD) growth of CNTs was performed with 2,500 sccm of methane, 10 sccm of ethylene, and 600 sccm of hydrogen at 900° C. for 10 min, resulting in allocation of oriented CNTs at specific positions.

(3) Metal electrode definition: Finally, metal electrodes (10 nm Ti and 30 nm Au) were defined using photolithography and lift off technique.

Following these procedures, the inventors successfully fabricated aligned nanotube biosensor arrays. The spacing between two adjacent devices was ~20 μm, and each device was clearly separated as is confirmed from the SEM images showing no nanotubes crossing between two devices.

Example 19

Making Nanosensors

Nanowire Fabrication

The fabrication consists of three steps: First, $In_2O_3$ NWs (previously grown on a $Si/SiO_2$ substrate via a laser ablation process developed previously) were suspended in isopropanol by sonication. The solution was then dispersed onto a complete 3" $Si/SiO_2$ substrate, followed by definition of the Ti/Au source and drain electrodes by photolithography. The interdigitated electrodes were designed to have channel length of 2.5 mm and effective channel width of 500, 780, and 2600 mm.

While the description above refers to particular embodiments of the present invention, it should be readily apparent to people of ordinary skill in the art that a number of modifications may be made without departing from the spirit thereof. The presently disclosed embodiments are, therefore, to be considered in all respects as illustrative and not restrictive. One skilled in the art will recognize many methods and materials similar or equivalent to those described herein, which could be used in the practice of the present invention. Indeed, the present invention is in no way limited to the methods and materials described.

---

The invention claimed is:

1. A method of preparing a nanosensor to detect DNA methylation, comprising:
providing a nanosensor; and
attaching a probe to the nanosensor,
wherein the probe is adapted to bind a methylated DNA sequence and an agent,
wherein the nanosensor is configured to detectably change in conductance when the methylated DNA sequence is itself bound by the agent.

2. The method of claim 1, wherein the nanosensor comprises nanotube and nanowire surfaces.

3. The method of claim 1, wherein the nanosensor is an NW/NT sensor.

4. The method of claim 1, wherein the probe comprises a polynucleotide.

5. The method of claim 1, wherein the probe is adapted to bind an agent.

6. The method of claim 5, wherein the agent comprises a signal amplifier.

7. The method of claim 1, wherein the probe comprises SEQ. ID. NO.: 1, SEQ. ID. NO.: 2, SEQ. ID. NO.: 3, SEQ. ID. NO.: 4, or a combination thereof.

8. The method of claim 1, wherein the probe comprises SEQ. ID. NO.: 5, SEQ. ID. NO.: 6, SEQ. ID. NO.: 7, SEQ. ID. NO.: 8, SEQ. ID. NO.: 9, SEQ. ID. NO.: 10, SEQ. ID. NO.: 11, SEQ. ID. NO.: 12, SEQ. ID. NO.: 13, or a combination thereof.

* * * * *

UNITED STATES PATENT AND TRADEMARK OFFICE
CERTIFICATE OF CORRECTION

PATENT NO. : 8,609,333 B2  Page 1 of 1
APPLICATION NO. : 12/680806
DATED : December 17, 2013
INVENTOR(S) : Zhou et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 264 days.

Signed and Sealed this

Twenty-second Day of September, 2015

Michelle K. Lee
*Director of the United States Patent and Trademark Office*